United States Patent [19]

Holzrichter et al.

[11] Patent Number: 5,620,854
[45] Date of Patent: Apr. 15, 1997

[54] METHOD FOR IDENTIFYING BIOCHEMICAL AND CHEMICAL REACTIONS AND MICROMECHANICAL PROCESSES USING NANOMECHANICAL AND ELECTRONIC SIGNAL IDENTIFICATION

[75] Inventors: John F. Holzrichter; Wigbert J. Siekhaus, both of Berkeley, Calif.

[73] Assignee: Regents of the University Of California, Oakland, Calif.

[21] Appl. No.: 402,800

[22] Filed: Mar. 13, 1995

Related U.S. Application Data

[63] Continuation of Ser. No. 111,445, Aug. 25, 1993, abandoned.

[51] Int. Cl.$^6$ .............. C12Q 1/68; G01N 33/53; G01N 21/00; C12P 19/34
[52] U.S. Cl. .............. 435/6; 435/5; 435/7.1; 435/7.9; 435/91.2; 436/182; 436/183; 250/559.32; 250/559.04
[58] Field of Search .............. 435/6, 5, 91.2, 435/7.1–7.9; 436/182, 183; 250/561

[56] References Cited

U.S. PATENT DOCUMENTS

| | | | |
|---|---|---|---|
| 3,648,513 | 3/1972 | Patterson | 73/53 |
| 3,989,383 | 11/1976 | Paulson | 356/96 |
| 4,172,379 | 10/1979 | van Tilburg et al. | 73/40.5 A |
| 4,269,068 | 5/1981 | Molina | 73/644 |
| 4,567,747 | 2/1986 | Matay | 73/1 D |
| 4,724,318 | 2/1988 | Binnig et al. | 250/306 |
| 4,766,083 | 8/1988 | Miyashita et al. | 436/517 |
| 4,902,892 | 2/1990 | Okayama et al. | 250/307 |
| 4,947,034 | 8/1990 | Wickramasinghe et al. | 350/507 |
| 4,992,659 | 2/1991 | Abraham et al. | 250/306 |
| 5,001,674 | 3/1991 | Kawasaki | 367/13 |
| 5,055,265 | 10/1991 | Finlan et al. | 422/82.05 |
| 5,106,729 | 4/1992 | Lindsay et al. | 435/6 |
| 5,144,148 | 9/1992 | Eigler | 250/492.3 |
| 5,155,359 | 10/1992 | Monahan | 250/306 |
| 5,200,051 | 4/1993 | Cozzette et al. | 204/403 |
| 5,225,064 | 7/1993 | Henkins et al. | 204/403 |
| 5,283,442 | 2/1994 | Martin et al. | 230/561 |
| 5,372,930 | 12/1994 | Colton et al. | 435/6 |

OTHER PUBLICATIONS

Homoma et al. Science 256:1180–1184, 22 May 1992.
Fraundorf et al Ultramicroscopy 37:125–129, 1991.
Hansma et al NAR 21:505 512 Feb. 1993.
Lee, Dissabs 53 (7B) 3632, 1992.
Lyubchencko – NAR 21, 1117–1123, Mar. 13, 1993.
Sensor Business digest (Sep. 1993) – cited as of interest.
Heckl, W.M. and J.F. Holzrichter, "DNA Base Sequencing", UCRL–JC–107970, Aug. 1, 1991.

*Primary Examiner*—W. Gary Jones
*Assistant Examiner*—Dianne Rees
*Attorney, Agent, or Firm*—Daryl S. Grzybicki; Henry P. Sartorio

[57] ABSTRACT

A scanning probe microscope, such as an atomic force microscope (AFM) or a scanning tunneling microscope (STM), is operated in a stationary mode on a site where an activity of interest occurs to measure and identify characteristic time-varying micromotions caused by biological, chemical, mechanical, electrical, optical, or physical processes. The tip and cantilever assembly of an AFM is used as a micromechanical detector of characteristic micromotions transmitted either directly by a site of interest or indirectly through the surrounding medium. Alternatively, the exponential dependence of the tunneling current on the size of the gap in the STM is used to detect micromechanical movement. The stationary mode of operation can be used to observe dynamic biological processes in real time and in a natural environment, such as polymerase processing of DNA for determining the sequence of a DNA molecule.

19 Claims, 4 Drawing Sheets

METHOD FOR IDENTIFYING BIOCHEMICAL AND CHEMICAL REACTIONS AND MICROMECHANICAL PROCESSES USING NANOMECHANICAL AND ELECTRONIC SIGNAL IDENTIFICATION

The United States Government has rights in this invention pursuant to Contract No. W-7405-ENG-48 between the United States Department of Energy and the University of California for the operation of Lawrence Livermore National Laboratory.

This is a Continuation of application Ser. No. 08/111,445 filed Aug. 25, 1993, now abandoned.

BACKGROUND OF THE INVENTION

1. Field of the Invention

The present invention relates to a method for measuring characteristic micromotions created by chemical, mechanical, optical, or electrical processes using scanning probe microscopy or laser interferometry. In particular, a stationary mode atomic force microscope is used to monitor microscopic dynamic processes, such as the replication of DNA for DNA sequencing.

2. Description of Related Art

The development of scanning probe microscopes in the 1980s, such as the scanning tunneling microscope and the atomic force microscope, provided the opportunity to locate and identify microscopic sites with atomic resolution. A wide variety of sites can be observed: small biological molecules that perform sophisticated biological functions, atomic sites on the surface of materials where corrosion, gasification, or catalytic reactions take place, and atomic sites where stress-induced fracture occurs.

The scanning tunneling microscope (STM) has a fine conducting probe that is held close to the surface of a site. Electrons tunnel between the site and the probe, producing an electrical signal. The probe is moved slowly across the surface and raised and lowered so as to keep the signal constant. A profile of the surface is produced, and a computer-generated contour map of the surface is generated. The technique is capable of resolving individual atoms, but requires conductive materials for image formation.

The atomic force microscope (AFM) also has a small probe that is held on a spring-loaded or flexible cantilever in contact with the surface of a site. The probe is moved slowly across the surface, and the tracking force between the tip and the surface is monitored. Forces as small as $10^{-13}N$ can be measured. The probe is raised and lowered so as to keep this force constant, and a profile of the surface is produced. Typically, a laser beam is bounced off the cantilever to monitor its position with angstrom-scale precision. Scanning the probe over the site at a constant force gives a computer-generated contour map of the surface. This instrument is similar to the STM, but uses mechanical forces rather than electrical signals. The AFM can resolve individual molecules and, unlike the STM, can be used with non-conducting samples, such as biological specimens.

A number of research groups, including ones at Lawrence Livermore National Laboratory, have attempted, with limited success, to use the scanning probe microscopes to sequence DNA by resolving individual nucleotide bases in tunneling images. Sequencing the human genome is one of the major scientific goals in the United States and in the world today. Dramatic improvements in human health and well-being will be possible by understanding the ordering of the billions of base pairs contained in DNA. Major research projects, like the Human Genome Project, have a need for improved techniques that will significantly reduce the analysis time of DNA fragments. The demands on the sequencing technology are even greater than the Genome Project because scientists also want to understand the DNA of different animals, plants, and microorganisms as quickly as possible.

Presently, the most common approach for sequencing the human genome is electrophoresis, which uses an electric field to separate fragments of DNA as they migrate through a sieving matrix (a gel). The DNA fragments are produced in a number of ways. The most widely employed method uses restriction enzymes, which act as molecular scissors, to sever the DNA at precise locations, producing a unique family of fragments for each enzyme used. The necessary number of DNA fragments are produced by biochemical reactions such as the DNA polymerase chain reaction (PCR), which can make millions of copies of a given DNA sequence. Unfortunately, these conventional electrophoresis techniques are relatively slow and costly, and time estimates for mapping or sequencing the entire human DNA molecule using these techniques range from decades to centuries.

Likewise, the use of STM and AFM in the conventional scanning or visualizing mode to sequence DNA presents problems. The normal process of raster scanning the microscope tip across the DNA molecules causes the molecules to move. In addition, the poor conductivity of the DNA precludes STM observation of the bases as attached to the phosphate backbone. The difficulty with the conventional AFM approach is that the radius of curvature of even the best AFM tips interferes with the identification of DNA bases.

U.S. Pat. No. 5,106,729 by Lindsay et al. describes a method for determining and visualizing the base sequence of DNA and RNA with a scanning probe microscope. The method replaces the oxygen in the DNA with a metal-sulfur complex, and passes the probe over the complexed polymer to measure and record the differences in electrical conductivity at preselected increments along the scanning path. Lindsay acknowledges the limitations of STM and AFM, caused by the distortion of the soft molecules as the tip touches them. Lindsay attempts to solve this problem by using the metal complex to enhance the electrical contrast in the STM.

However, an urgent need exists for a DNA sequencing technique that is faster than the conventional electrophoresis techniques, and that does not require biochemical labeling or complexing the DNA molecule in order to image the base sequence. This invention addresses these challenges in particular, and introduces a general technique for detecting and measuring micromotions caused by an unlimited variety of chemical, mechanical, optical, and electrical processes.

SUMMARY OF THE INVENTION

This invention is a method for detecting microchemical reactions or micromechanical processes by measuring the characteristic signals emitted during a time sequence of the reactions using stationary mode operation of scanning probe microscopes. The signals may be detected directly, or may be transmitted through a medium and received indirectly. The method can be applied to any kind of reaction or process that produces vibrations, including biomechanical, biochemical, and inorganic reactions, and electrical, optical, and mechanical processes. The method greatly extends the range of information that is gathered with a scanning probe microscope.

The approach of this invention is to use the scanning probe microscope in a conventional way to locate or image a site where a process of interest occurs. The scanning probe is then used in a stationary mode to position a microdetector on or near the site. The probe detects and processes the signals (micromechanical, acoustic, electronic, optical, chemical) that are emitted directly from the site or that are transmitted (indirectly) through the surrounding medium. This latter approach is a type of acoustic detection. A micromechanical detector, such as the tip of an atomic force microscope (AFM) or a scanning tunneling microscope (STM), when held stationary can detect characteristic pulsations, configurational changes, charge fluctuations, or phonon emissions associated with a local chemical or mechanical event. An advantage of the AFM is its routine use in liquid environments, including reacting environments; however, the AFM has only been used in the scanning mode, and not in the stationary mode as described in this invention.

The invention is based on the direct micromechanical, acoustic, electronic, or chemical reception of information and identification of a time sequence of chemical or micromechanical reactions. A micromotion detector directly or indirectly monitors a process by reading the force waves (e.g., direct or acoustic pulses) that originate at a reaction site and are transmitted directly or through a fluid or other medium surrounding or coupled to the process. The detection efficiency of the process depends on the source transmitting the mechanical motions with sufficient intensity and fidelity that the detector receives a signal that can be distinguished from the background noise. In the case of detection through a surrounding medium, the coupling to the medium and the medium transmission are important properties. Other detectors may monitor electronic or chemical signals generated during this process.

Many important biological and inorganic processes occur at acoustic rates (~10–100 reactions per site per second), and these reactions may lead to new molecular structures. The creation of new structures generates structural or fluid motions in the environment that are characteristic of the structure being created. The present method can identify a characteristic signature created by the presence or absence of normal or abnormal processes in a living organism, in a cell, or in a subunit of a cell. The method can receive information on catalytic processes, or on the extraction of information from a chemical template (possibly leading to a new structure). The invention can be used to monitor micromechanical processes such as fracture, or biomechanical functions such as breathing or other metabolic processes in very small creatures. These events are detectable using the present method when the events occur at suitable rates, typically between 10–1000 Hz, and if they occur with suitable amplitudes.

The method is applied to structures as small as a single molecule, and therefore can provide information about biochemical processes such as egg fertilization, viral attack on a cell, the operation of mitochondria, and other biochemical sequences occurring during the normal operation of cellular structures. Of particular interest is the monitoring of genetic processes, such as DNA unwinding during cell replication, reading DNA in situ during normal or abnormal workings of a cell, enzyme processing of DNA, RNA processing, and reading messenger RNA (which generates proteins). Catalytic reactions, including biochemical catalysts (enzymes) and inorganic catalysts (e.g., zeolite catalysis of hydrocarbons), can be studied using the present method. Biological events can be measured in situ or separate from their natural host, as long as the techniques allow the desired process to continue and satisfy measurement criteria.

In addition to the motion measuring device and the structure that catalyzes or promotes the formation of a new molecular species, a method to couple the vibrations to the detector is required. This may be a substrate to support the structure, with direct or indirect contact of the micromechanical detector to the structure promoting the chemical process. In the case of measuring cellular processes such as viral invasion, simple contact to the cell surface will suffice. In the case of detecting enzymatic promotion of a chemical or biochemical reaction, such as DNA copying, direct contact with the enzyme surface may be used.

The approach provided by the present invention has the potential to sequence DNA at a rate ten to one hundred times faster than the presently used gel methods. Dramatic reductions in time and cost for sequencing DNA would result, which will significantly improve the progress of the Human Genome Project. This new technique can also be applied to a wide variety of other enzyme studies, as well as to micro-acoustic detection in non-destructive testing and seismology. In addition, more (if not all) of the sequence structure of the DNA molecule may be accessible with this method, which is not true of present sequencing methods.

DETAILED DESCRIPTION OF THE INVENTION

General Description

The present invention is a method for detecting motions on a microscopic level that are created by a variety of reactions and processes, including micromechanical, microchemical, microbiological, micro-optical, and microelectrical. This method uses a scanning probe microscope in a stationary mode to gather information at a molecular scale and smaller. The method measures vibrations created by local mechanical events, such as microcracking, or by chemical processes, such as catalysis, DNA replication, or cellular viral attack.

A scanning probe microscope, such as the AFM or STM, is typically used to image or visualize a physical structure by scanning. However, the present method uses the instrument in a stationary mechanical mode, whereby the probe's tip measures characteristic motions (vibrations) or acoustic signals (frequencies) created or emitted by a specific site. Using the probe in a stationary mode allows one to "listen" to the locally-emitted micromotions at sites on a micrometer to nanometer scale; consequently, this technique is referred to as "nanostethoscopy". The stationary mode minimizes the problems associated with conventional scanning probe microscopes; in particular, this mode eliminates lateral sample distortion or deformation.

The micromotions created by a chemical structure or process can be detected by the probe in at least three ways. The probe can be used to detect movements of a structure of interest directly. That is, the probe tip physically touches the structure that will produce characteristic movements and measures the motions as the structure undergoes some kind of process (chemical, biological, mechanical, electrical, optical). These motions may include the change in configuration of an enzyme, movement of an inorganic catalyst, expansion of a microcrack, or the expansion and contraction of a material caused by temperature or electrical changes.

Second, the probe can be used to detect micromotions indirectly, by receiving signals that are transmitted from a site through a medium, such as a fluid or a solid. The motions in the medium propagate away from the source for a distance to the detector and are caused by the same kinds of processes described above. The detector may also measure time-varying motions caused by incoming or outgoing chemical products in a reaction.

Third, an intermediary site may be attached to a site of interest, and the probe can be used to detect the physical movements of the intermediary site, which in turn are caused by motions of the primary site. Instead of using a scanning probe microscope, the technique of laser interferometry could be used to detect the motions of the intermediary site. For example, an enzyme could be attached to a membrane, and the enzyme will recognize input products or a template and then fabricate a product or products. The enzyme motions cause vibrations in the surrounding liquid and in the membrane, which serves as a reflector to interferometrically detect the motions. In another example, a gold ball could be attached to an enzyme, which would move as the enzyme moved. A light signal could detect the motions interferometrically.

Specific Description

Figure 1A:
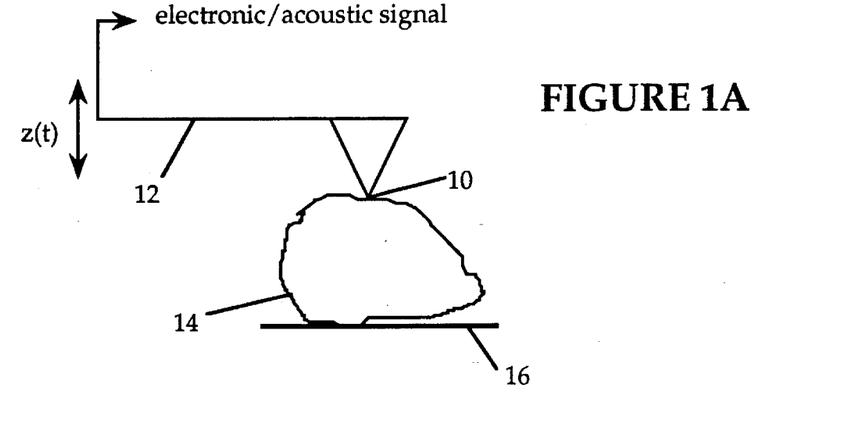
FIGS. 1A, 1B, and 1C are schematic diagrams showing the positioning of a cantilever-tip assembly on or near a site of interest according to the present invention.
Figure 1B:
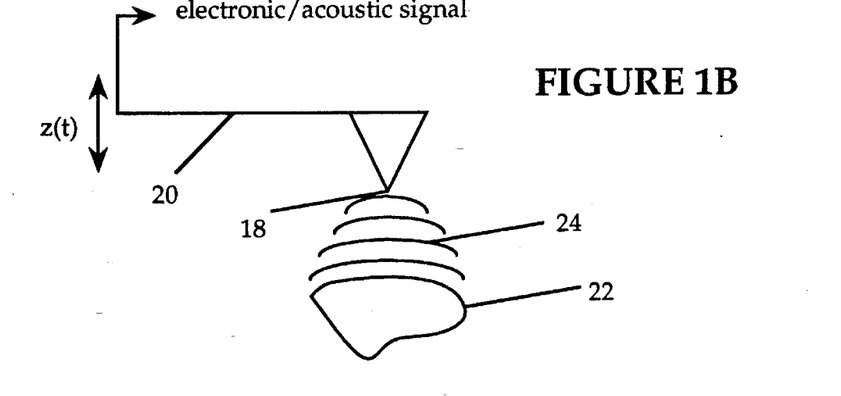
Figure 1C:
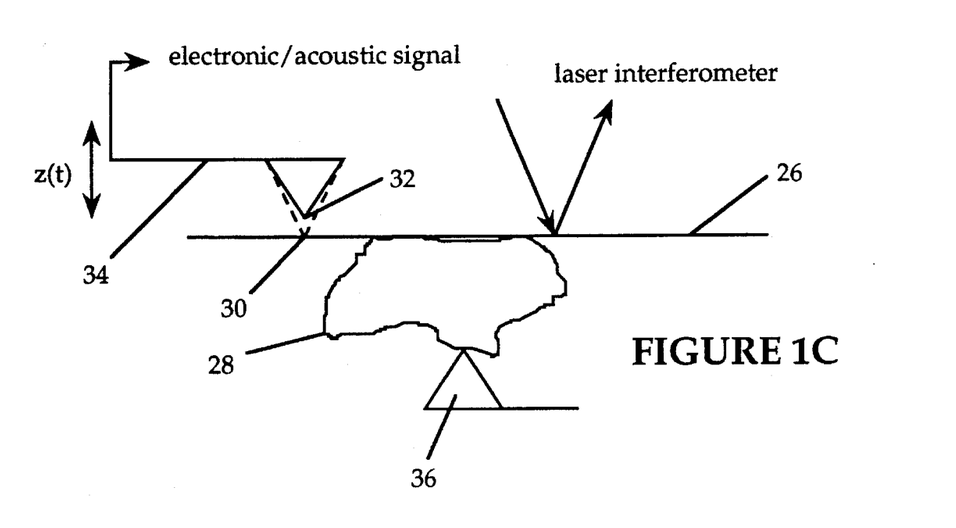

The present method is illustrated schematically in FIGS. 1A–1C. A specific site of interest is first located using a location detector, such as a tip of an AFM or a STM probe. The site may be attached to a substrate for support. Attachment to a substrate is typical for biological and chemical applications. After the site is located, a motion detector is positioned at the site. This detector may be the same AFM or STM tip used as the location detector, but the mode is changed to keep the tip stationary to detect micromotions emitted from the site. Alternatively, a separate, second detector may be used as a motion detector to measure time-varying qualities at the site (movements in vertical motion, acoustic or sound waves) or changes in the system (comparing motion at two times).

FIG. 1A shows the tip 10 of an AFM or STM cantilever 12 positioned on a structure site 14 of interest, which may be attached to a substrate 16 for support. The cantilever 12 moves vertically as a function of time (z(t)) as the site 14 undergoes chemical, mechanical, optical, or electrical changes. The physical movements of the cantilever 12 are converted into an electrical signal, which is compared to the signal obtained when the structure site 14 is not undergoing the process of interest.

FIG. 1B shows the tip 18 of the cantilever 20 positioned at a distance from the structure site 22. The site 22 is surrounded by a medium (gas, liquid, or solid) that transmits acoustic or sound waves 24 caused by micromotions at the site 22. The site 22 may change physical configuration, or undergo chemical reactions or changes in electrochemical potential, or experience mechanical, optical, or electrical transformations, which generates pressure waves 24 that propagate through the medium across the distance between the site 22 and the tip 18 (detector). The deflections of the tip 18 are converted electronically to measure characteristic vibrations front the structure site 22.

FIG. 1C illustrates a third way to measure distinctive vibrations caused by activity at a selected site. An intermediary site 26, such as a membrane as shown or a gold sphere, is attached to the primary site 28. A counter-mass, or another substrate, or another probe tip 36 as shown is typically in contact with or attached to the back of the primary site 28 for support. The tip 30,32 of the cantilever 34 is positioned at or near the intermediary site 26 to detect micromotions that originate at the primary site 28 and then are transmitted to the intermediary site 26.

As in FIG. 1A, the tip 30 may detect vibrations by sitting directly on the intermediary site 26. Alternatively, the movements of the primary site 28 may be conveyed to the intermediary site 26, as in FIG. 1B. The physical movements of the intermediary site 26, in turn, create acoustic waves that are transmitted through the surrounding medium to the tip 32, and thus the motions of the primary site 28 are detected indirectly. Another alternative is to use the intermediary site 26 as a reflector for laser interferometric detection of movements caused by vibrations in the primary site 28.

The present method has a wide variety of possible applications, as summarized below.

A. Cellular Properties

Any vibrational phenomenon associated with normal or abnormal cell functioning can be monitored using the present technique, in the same way that the function of internal organs, such as the heart or lungs, in biological organisms is monitored by placing a listening device like a stethoscope near the organ's surface. Time-dependent cell functions, such as conformational changes, appendage motion, replication (cell division), viral attack (membrane motion), or the effect of drugs or toxins, may be detected. The unusually rapid cell division of cancer cells may be identifiable.

The AFM or STM probe tip is placed either directly on structures on or in the cell, or is positioned at a distance to monitor cellular movement. One advantage of this method is that measurements are taken in the natural fluid environment of the cell at the same time as the cellular activity.

B. Operation of Enzymes (Catalysis of Reactions)

The present method can be used to investigate the interaction of a biological catalyst with the substrate. This method may be used to study the intermolecular transfer of phosphate in skeletal muscle enzymes, the interaction of proteins and ligands, and the unfolding and refolding of proteins. Of particular interest are polymerases, which catalyze reactions with DNA and RNA. These measurements can be done in at least three ways: (a) directly touching the enzyme while it works on the substrate; (b) indirectly listening to the interaction of the enzyme and substrate; and (c) attaching an intermediary site to the enzyme and then measuring the motion of the intermediary site using scanning probe microscopy or laser interferometry.

C. Integrated Circuits

The present method can be used to examine integrated circuits (ICs) and microprocessing chips. For example, as electric current flows through the conductive material making up the IC, the material increases in temperature and expands, causing physical motion that can be detected by the AFM or STM tip. This method can detect the location and the type of failures that occur, and can characterize the local physical changes on a nanometer scale. Example III describes the measurement of 2 Å changes in a gold conductor in an integrated circuit on a silicon chip.

D. Fractures

In materials science and engineering, the performance and failure of structural elements under a load can be assessed by acoustically monitoring the fracture. Using this same concept on a much smaller scale, the site of interest may be a cracking tip which, when stressed, will expand outward, creating acoustic vibrations that can be detected by an AFM or STM. The propagation of the crack under mechanically stressed conditions can be monitored and the behavior of materials under stress can be studied.

E. DNA Sequencing

Figure 2:
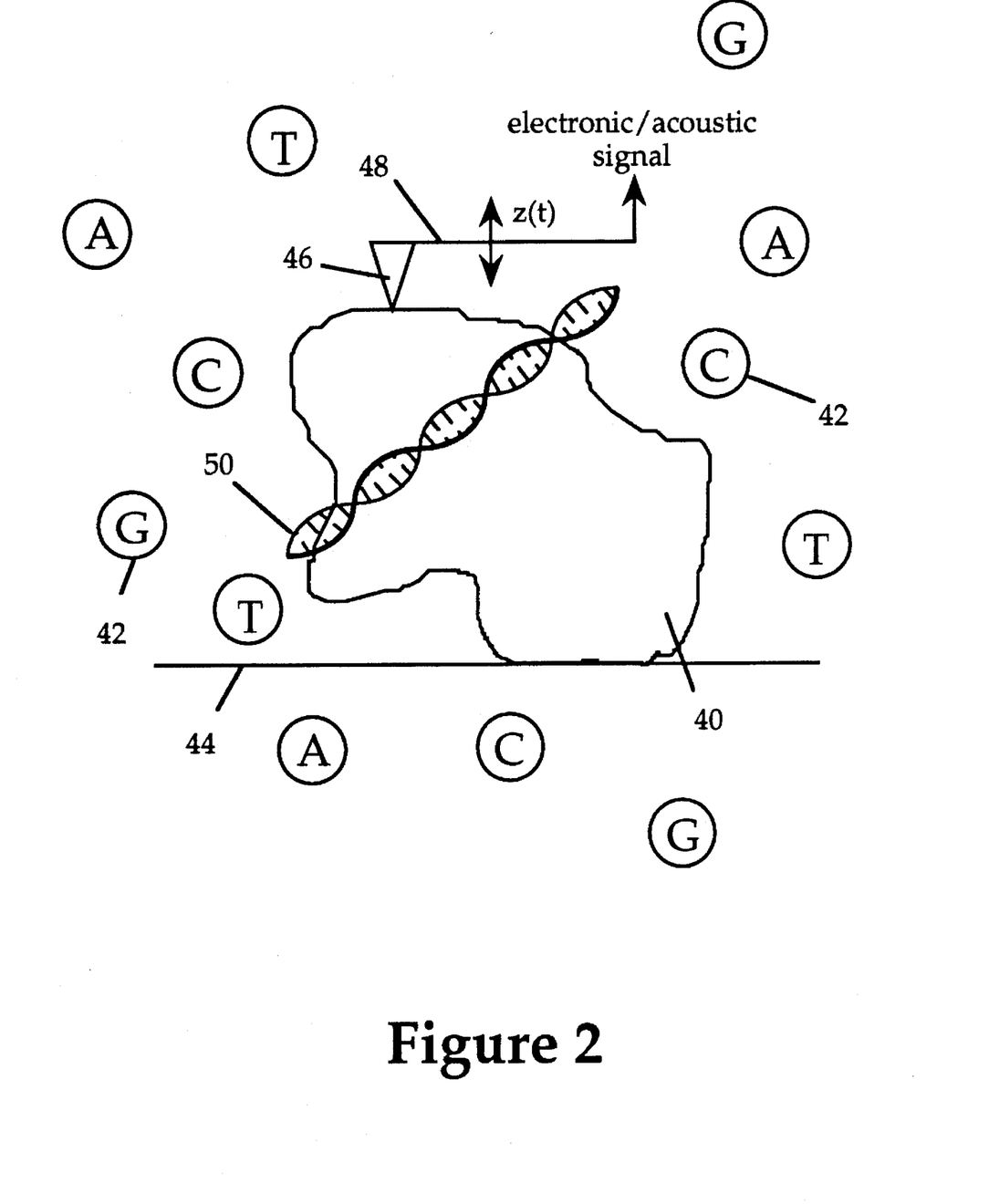
FIG. 2 shows schematically the method for monitoring the processing of DNA by polymerase directly using the tip of the probe.

A specific application of the present method is to sequence DNA by monitoring polymerase processing of DNA by measuring the different acoustic signals the enzyme emits while copying different nucleotide bases. FIG. 2 is a schematic diagram of this process. The measurements take place in a liquid cell that contains a solution of the DNA polymerase 40 and selected concentrations of the nucleotide bases 42 (A,T,C,G) in a liquid medium. The enzymes 40 are attached or fixed to a suitable substrate 44 surface either by natural forces or using conventional, although not trivial, techniques, such as organic glue.

An AFM is typically used as the scanning probe and is operated in two ways. First, the AFM is used in the conventional way to search for and image one of the fixed polymerase molecules 40 in the liquid environment. In the second and unconventional use of the AFM, the tip 46 at the end of the cantilever 48 is positioned stationary on top of the polymerase 40 to monitor the deflections that occur as the enzyme 40 operates on a DNA molecule 50 (or fragments thereof). The cantilever 48 detects the changes in configuration of the enzyme 40 as a function of time during its interaction with the DNA fragments 50 and nucleotide bases 42.

Figure 3:
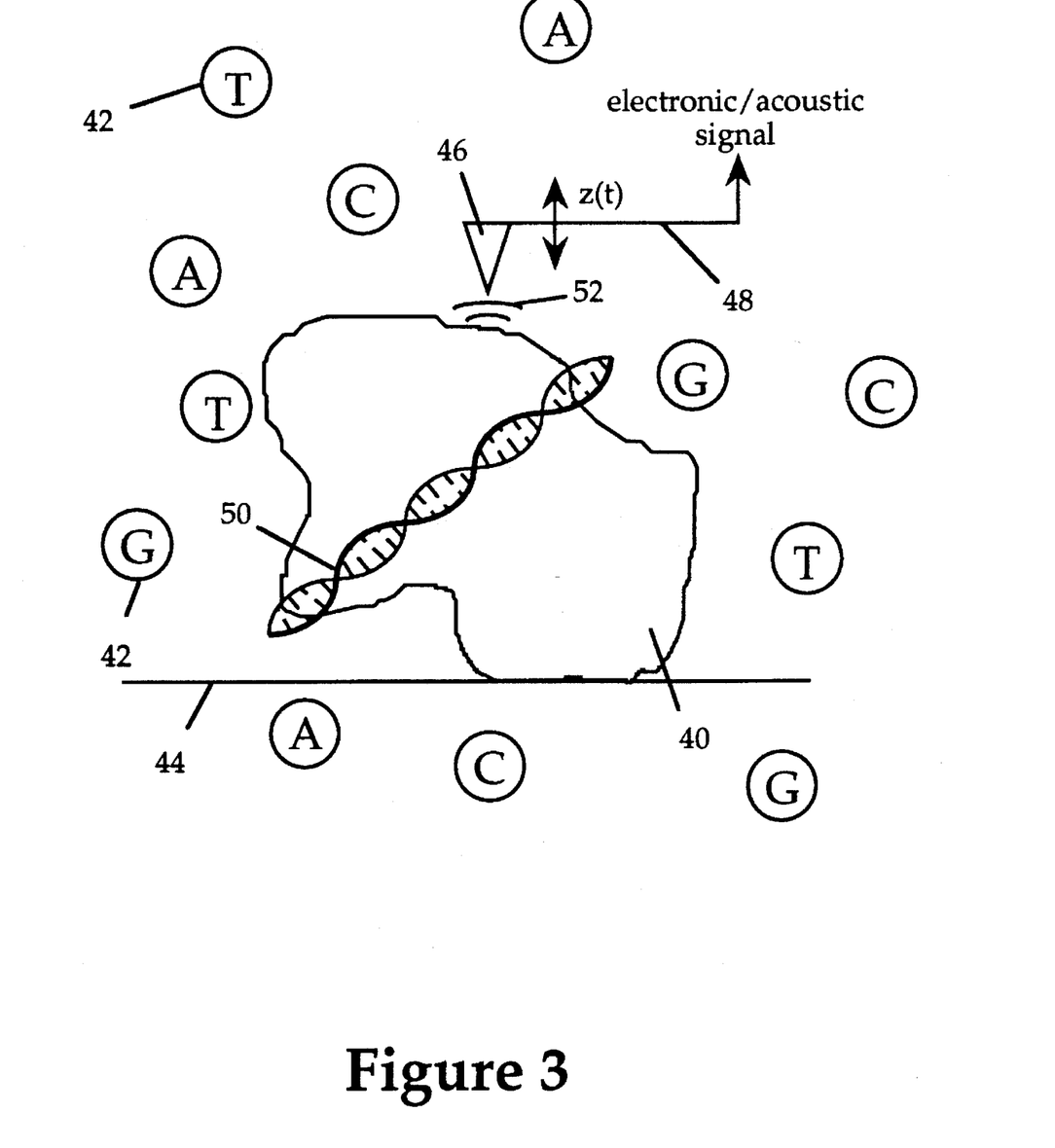
FIG. 3 shows the method for indirectly monitoring polymerase processing of DNA through a surrounding medium.
Figure 4:
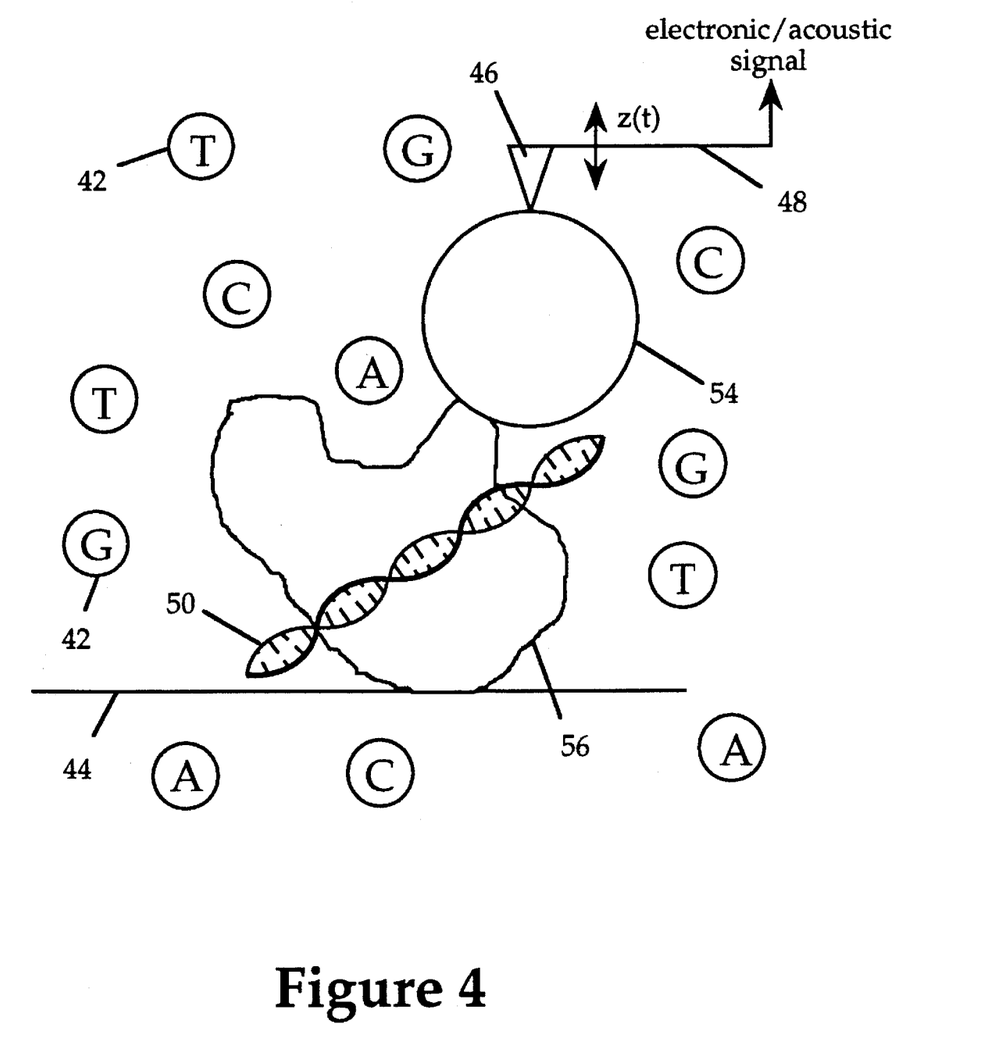
FIG. 4 is a schematic diagram of the method for indirectly monitoring the processing of DNA by detecting micromotions of an intermediary site that is attached to the processing enzyme.

The AFM probe can measure the enzyme's movements in at least two other ways. As shown in FIG. 3, the probe tip 46 may be positioned at a distance from the enzyme 40 to detect the pressure or acoustic waves 52 that are transmitted through the liquid and created by the interactions of the polymerase 40 and DNA 50. Alternatively, as shown in FIG. 4, an intermediary site 54 such as a gold sphere is attached to the enzyme 56. The motions of the intermediary site 54 may be measured using the AFM probe as shown, by direct contact of the tip 46 with the intermediary site 54; thereby, the enzyme's movement via the intermediary site is detected. The movements of the intermediary site 54 may also be measured directly using laser interferometry, or indirectly by detecting acoustic waves transmitted through the liquid medium.

The polymerase starts to process the DNA after the DNA segments are introduced into the liquid cell. The DNA segments are biochemically prepared using conventional methods, such as PCR, to produce known lengths or templates of a known or unknown sequence. The DNA segments approach the enzyme, which processes the nucleotide bases. The activity of the enzyme can be started and stopped using conventional methods (e.g., blockers).

The objective is to use the extremely sensitive cantilever of the AFM as an "ear" to listen to the function of a biological entity, analogous to the use of a stethoscope to monitor the function of a heart. Charge fluctuations that occur during sequencing can be monitored electronically at the same time. This method monitors the enzyme as it undergoes some structural or electrical rearrangement while processing the bases of DNA. If the rearrangement has characteristic features in amplitude, time, or both together that are specific to each base, then distinguishable signals can be obtained for the four nucleotide bases: adenine, cytosine, thymine, and guanine. The different bases processed by the enzyme during reaction with the DNA segment are identified to determine the base sequence of the DNA strand being copied.

Thermal or concentration-induced noise will limit the sensitivity, but will not preclude the described method. Typically, monitoring is performed in a thermally stabilized environment to eliminate temperature-induced drift. However, the temperature or the chemical environment may be changed to slow down rates of reaction to better identify a sequence of reactions.

Micromechanical (acoustic) frequencies can be monitored in the frequency range of about 1–10 kHz and are limited by the characteristics of the cantilever. (Changes in cantilever design can lead to a greater range of frequencies.) This range is much lower than the frequency of vibration of individual atoms in a biological molecular entity, but is higher than those associated with typical biological DNA processing speeds of 30–50 bases per second. If electrical activity is the studied signal, then electrical responses can be measured to frequencies as high as 1 MHz; thus, electrical activity may be measurable at higher speeds than present micromechanical motions.

Since the duplicating process is performed repeatedly by the same enzyme, this technique of sequencing by monitoring the function of a DNA-processing biological molecule with an atomic force cantilever (or electronic or chemical effect detector) can automatically acquire statistics if many identical DNA segments are monitored or they are replicated. Monitoring can be terminated once sufficient data are acquired. The consistency of the reactions and rates of mutation may be studied.

Different concentrations of the nucleotide bases in solution may be used to control the amount of time for interaction of the base with the enzyme. The proportion of a particular base in the solution of four bases determines the probability of the enzyme reacting with that base. Thus, if the concentration of adenine is the highest, then on average the time for the polymerase to begin to react with adenine should be the shortest. Once the base is bound to the enzyme, a separate time sequence is followed that provides additional information.

EXAMPLE I. DNA NANOSTETHOSCOPY

The present method is used to monitor the catalytic reactions of the enzyme *E. Coli* DNA-Polymerase I during DNA replication. This enzyme is an excellent system for studying DNA polymerases and template-directed DNA synthesis since high resolution structural information exists. The enzymes are attached to a smooth substrate by conventional means, and the AFM is used in the conventional scanning mode to locate and position the tip on a single enzyme molecule. The tip is used to detect the conformational changes of the enzyme as it processes and replicates a segment of DNA by adding bases (nucleotides) to the template-primer. DNA may be sequenced by "listening" as individual nucleotide bases are incorporated into a DNA molecule.

The procedure is to immobilize a subunit of the enzyme, such as the Klenow fragment, onto a smooth surface, in the presence of a buffered liquid containing the DNA fragments of interest and the nucleotide reactants (bases) needed for DNA replication. The goal is to identify characteristic signals for forming an adenine-thymine nucleotide pair and a guanine-cytosine pair.

In the same manner as shown in FIG. 2, the AFM's cantilever tip is positioned on the Klenow fragment. As replication proceeds, energy is released and the enzyme-DNA complex changes configuration. The rate-limiting step of the polymerase reaction is ascribed to a conformational change in the enzyme-DNA-base complex. The energy associated with this change will produce a force that will move a sufficiently compliant probe tip. The tip motion will be detected as a signal in the low frequency acoustic range associated with the nominal room temperature rate of replication, approximately 15–50 Hz.

The polymerase reaction is a complex, multi-step process. A kinetic mechanism has been proposed for the incorporation of nucleotides into DNA catalyzed by the Klenow fragment. The overall free energy change of a single nucleotide incorporation cycle during processive DNA polymerization has been measured as ~2.5 kcal/mole. This energy, if associated with a unidirectional configurational change, can result in a displacement of the AFM cantilever/spring of up to ~6 Å. This analysis is based on a typical cantilever spring constant of ~0.1N/m. Laser-based optical detection techniques used in AFM measurements are capable of measuring cantilever deflections on the order of 0.1 Å. Thus, detection of the polymerase reaction is possible using the present method.

The estimated force generated by the polymerase reaction is on the order of 60 pN, which is an order of magnitude greater than the recently measured forces associated with biological motors, but is consistent with the energy available for the motion in an enzyme. In addition, images of biomolecules have been obtained by other workers using forces of this magnitude in a liquid environment. This value is approximately the recommended deformation threshold of $10^{-11}$N for AFM of biological molecules. Finally, the force exerted by the enzyme onto the tip due to the polymerase reaction is calculated to produce an overall enzyme deformation of ~0.65 Å, or about 1% of the Klenow fragment diameter. This level of deformation should not affect enzyme activity.

Heat deposited by the laser can induce thermal noise in the liquid environment, which may limit measurement sensitivity. Cantilever displacement due to thermal noise may represent as much as 35% of the signal for the polymerase reaction. Nonetheless, using optical techniques, RMS vibrational noise levels of less than 1 Å have been measured for an AFM tip placed onto a biological substrate. Further noise reduction may be accomplished by statistical techniques and by using an integrated strain-gauge cantilever, which operates without introducing laser-generated heat.

EXAMPLE II. VIBRATIONS OF A LIVING BIOLOGICAL SUBJECT

The present method is used to detect the micrometer-scale vibrations caused by wing beating of artemia shrimp pre-nauplius while emerging from an encapsulated cyst. The brine shrimp can survive for years in the cyst, but emerges after contact with seawater and light. Because of its convenient size (180 micrometer diameter) and the ease of initiating its development, brine shrimp are an important experimental system of developmental processes and time-dependent functionality of various organs.

Shrimp cysts are placed onto a microscope slide with salt solution to form the bottom of a fluid cell. The tip of the atomic force microscope is placed onto a selected shell, and images are taken as the shell cracks. After the pre-nauplius stage is formed, the tip is repositioned onto a location behind the right eye-spot and held stationary (analogous to FIG. 1A). Strong pulsations are observed just before the shrimp leaves the shell having an amplitude of about 3 µm and a frequency of about 10 Hz. The nanostethoscope can be used to determine the location, the time during development, and the amplitude and frequency of vibrations occurring in a living biological entity.

EXAMPLE III. MECHANICAL MOTIONS IN AN ELECTRONIC CIRCUIT

Micrometer size metallic interconnect lines in electronic circuits are heated by the electric current passing through them, and expand according to their thermal expansion coefficient. Hence a gold circuit one micrometer in height expands by 0.14 nm when its temperature rises 10° C. A microelectronic circuit is fabricated on a silicon chip (thickness of 0.55 mm) having a pattern of three gold lines with a cross-section of 1 µm² and a length of about 50 µm.

Each of the lines is attached to a wide gold bar and to an external electronic circuit capable of generating square waves over a range of frequencies. The chip is mounted in the nanostethoscope (AFM) and imaged to find the location at which to monitor the thermal expansion. Adiabatic calculations predict that at a current of about 3 mA, the temperature of each gold line should reach 25° C. in about 5 msec. Hence, frequencies in the 1 kHz range can be investigated, which is well within the capability of the nanostethoscope's electronics.

The tip of the AFM is placed at the location of the 1 µm bar for imaging. The tip is then held stationary in a position atop the bar, and the deflections of the cantilever (to which the tip is attached) are monitored as a function of time. The configuration is shown in FIG. 1A, with the primary site 14 being the gold conductor. An applied square wave voltage is switched on and off, which in turn generates an electronic/mechanical noise that is converted to a visual display. The deflections of the cantilever as a function of time are quantified. The time-dependent expansion (vibration) of the gold bar can be identified as having a frequency of about 15 Hz and an amplitude of about 0.2 nm, which corresponds to a temperature-oscillation of approximately 14° C.

The RMS noise while the square wave oscillator is off is about 0.037 nm. Therefore, the nanostethoscope can identify 0.2 nm oscillations (vibrations) with a signal/noise ratio of about six (6). This example demonstrates that the AFM can detect vibrations at the angstrom level, lending itself to submicrometer spatial analysis of the thermal performance of electronic circuits.

The foregoing description of preferred embodiments of the invention is presented for purposes of illustration and description and is not intended to be exhaustive or to limit the invention to the precise form disclosed. Many modifications and variations are possible in light of the above teaching.

We claim:

1. A method for detecting time-varying motions created on a microscopic scale using a scanning probe microscope having a physical tip for mechanical signal identification, comprising:

(a) locating a single site comprising a molecule or molecules of interest having microscopic dimensions by using the scanning probe microscope in a locator mode, wherein the molecule or molecules have time-varying motions due to a biological, chemical, mechanical, optical, or electrical process;

(b) positioning the physical tip of the scanning probe microscope in a stationary mode at the single site; and (c) monitoring physical movements of the tip as a function of time as the process occurs by using the scanning probe microscope in a stationary, non-scanning mode, thereby detecting micromotions created at the site.

2. The method as recited in claim 1, further comprising positioning the tip in physical contact with at least one molecule at the site, and wherein the physical movements of the tip are caused by micromotions of the molecule.

3. The method as recited in claim 1, further comprising surrounding the site with a transmitting medium, and positioning the tip in physical contact with the medium, wherein the micromotions created at the site are transmitted through the medium as acoustic or pressure waves, and the physical movements of the tip are caused by the waves.

4. The method as recited in claim 1, further comprising attaching at least one molecule at the site to a supporting substrate.

5. The method as recited in claim 1, wherein the scanning probe microscope is selected from the group consisting of atomic force microscopes and scanning tunneling microscopes.

6. The method as recited in claim 1, further comprising attaching an intermediary body to at least one molecule at a site of interest, whereby the micromotions of the site of interest cause micromotions at the intermediary body, and wherein the physical movements of the tip are caused by micromotions created at the intermediary body.

7. The method as recited in claim 6, further comprising positioning the tip in physical contact with the intermediary body, and wherein the physical movements of the tip are caused by micromotions of the intermediary body.

8. The method as recited in claim 6, further comprising surrounding the intermediary body with a transmitting medium, and positioning the tip in physical contact with the medium, wherein the micromotions created at the intermediary body are transmitted through the medium as acoustic or pressure waves, and the physical movements of the tip are caused by the waves.

9. The method as recited in claim 6, wherein the intermediary body is selected from the group consisting of a membrane and a chemically inert metallic sphere.

10. The method as recited in claim 1, wherein the tip comprises a tip and cantilever assembly.

11. The method as recited in claim 1, wherein the site is an enzyme having polymerase activity.

12. The method as recited in claim 1, wherein the site is a living cell.

13. A method for detecting time-varying motions created on a microscopic scale by an enzyme using a scanning probe microscope having a physical tip for mechanical signal identification, comprising:

(a) attaching an enzyme to a supporting matrix, wherein the enzyme is in solution and has time-varying micromotions due to interaction with a substrate;

(b) locating the enzyme and positioning the physical tip of the scanning probe microscope in a stationary mode at the enzyme;

(c) introducing the substrate into the solution, wherein the solution is allowed to come to rest and the substrate and the enzyme interact; and (d) monitoring the physical movements of the tip as a function of time as the interaction occurs, by using the scanning probe microscope in a stationary, non-scanning mode, thereby detecting micromotions caused by the enzyme's interaction with the substrate.

14. The method as recited in claim 13, further comprising positioning the tip in physical contact with the enzyme, and wherein the physical movements of the tip are caused by micromotions of the enzyme.

15. The method as recited in claim 13, further comprising surrounding the enzyme with a transmitting medium, and positioning the tip in physical contact with the medium, wherein the micromotions created at the enzyme are transmitted through the medium as acoustic or pressure waves, and the physical movements of the tip are caused by the waves.

16. The method as recited in claim 13, further comprising attaching an intermediary body to the enzyme, whereby the micromotions of the enzyme cause micromotions at the intermediary body, and wherein the physical movements of the tip are caused by micromotions created at the intermediary body.

17. The method as recited in claim 16, further comprising positioning the tip in physical contact with the intermediary body, and the physical movements of the tip are caused by micromotions of the intermediary body.

18. The method as recited in claim 16, further comprising surrounding the intermediary body with a transmitting medium, and positioning the tip in physical contact with the medium, wherein the micromotions created at the intermediary body are transmitted through the medium as acoustic or pressure waves, and the physical movements of the tip are caused by the waves.

19. A method for detecting time-varying motions created on a microscopic scale using a scanning probe microscope having a physical tip for mechanical signal identification, comprising:

(a) locating a single site comprising a molecule or molecules of interest having microscopic dimensions by using the scanning probe microscope in a locator mode, wherein the molecule or molecules have time-varying motions due to a biological, chemical, mechanical, optical, or electrical process;

(b) attaching an intermediary body to the site of interest, whereby micromotions of the site of interest cause micromotions at the intermediary body; and (c) monitoring the physical movements of the intermediary as a function of time as the process occurs using laser interferometry, thereby detecting micromotions created at the site.

* * * * *